United States Patent
Hattori

(10) Patent No.: US 9,625,407 B2
(45) Date of Patent: Apr. 18, 2017

(54) CATALYSIS COMBUSTION TYPE GAS SENSOR

(71) Applicant: Yamaha Fine Technologies Co., Ltd., Shizuoka-ken (JP)

(72) Inventor: Atsuo Hattori, Iwata (JP)

(73) Assignee: Yamaha Fine Technologies Co., Ltd., Hamamatsu (JP)

( * ) Notice: Subject to any disclaimer, the term of this patent is extended or adjusted under 35 U.S.C. 154(b) by 0 days.

(21) Appl. No.: 14/853,544

(22) Filed: Sep. 14, 2015

(65) Prior Publication Data

US 2016/0077032 A1 Mar. 17, 2016

(30) Foreign Application Priority Data

Sep. 16, 2014 (JP) ................. 2014-187772

(51) Int. Cl.
  *B01J 10/00* (2006.01)
  *G01N 27/16* (2006.01)
  *G01N 33/00* (2006.01)

(52) U.S. Cl.
  CPC ......... *G01N 27/16* (2013.01); *G01N 33/0027* (2013.01)

(58) Field of Classification Search
  CPC .......................... B01J 19/10; B01J 19/0013
  USPC ................................ 422/643, 603
  See application file for complete search history.

(56) References Cited

U.S. PATENT DOCUMENTS 5,393,351 A * 2/1995 Kinard ............... H01L 35/08
                                                    136/200
2013/0209315 A1   8/2013 Kimura

FOREIGN PATENT DOCUMENTS

| JP | 2001-99801 A | 4/2001 |
| JP | A-2005-156364 | 6/2005 |
| KR | 10-2004-0092226 A | 11/2004 |
| WO | WO 2012/033147 A1 | 3/2012 |

OTHER PUBLICATIONS

Office Action from KR Application No. 10-2015-0119572 mailed Aug. 16, 2016.

* cited by examiner

*Primary Examiner* — Natalia Levkovich
(74) *Attorney, Agent, or Firm* — Blank Rome LLP

(57) ABSTRACT

A catalysis combustion type gas sensor that detects an inflammable gas includes a heat-insulating portion; a heater that is formed on the heat-insulating portion; a gas reaction film that is formed on the heater on the heat-insulating portion and includes a carrier carrying a combustion catalyst for the inflammable gas; a temperature-measuring element that is formed in the vicinity of the gas reaction film on the heat-insulating portion; and a soaking portion that is formed on the heat-insulating portion and is arranged between the heat-insulating portion and the gas reaction film. The soaking portion is configured so as to decentralize heat transferred to the soaking portion in the entire soaking portion.

5 Claims, 10 Drawing Sheets

CATALYSIS COMBUSTION TYPE GAS SENSOR

BACKGROUND OF THE INVENTION

Field of the Invention

The present invention relates to a catalysis combustion type gas sensor that detects an inflammable gas, and particularly, to a technique that makes the detection sensitivity of the inflammable gas higher in the catalysis combustion type gas sensor.

Priority is claimed on Japanese Patent Application No. 2014-187772, filed Sep. 16, 2014, the content of which is incorporated herein by reference.

Description of Related Art

In the related art, catalysis combustion type gas sensors, which combust an inflammable gas by using a catalyst and electrically detect a rise in the temperature of the catalyst caused by combustion heat, have been used as gas sensors that detect inflammable gases, such as hydrogen. Even in such catalysis combustion type gas sensors, similar to various sensors, it is always required to make the detection sensitivity higher, and high sensitivity is achieved by various methods. For example, Japanese Unexamined Patent Application No. 2001-99801 suggests that, in order to enhance gas detection sensitivity with respect to a low-concentration inflammable gas or an inflammable gas with low sensitivity, a heater for promoting combustion of the inflammable gas is formed in the vicinity of a catalyst layer (gas detection film) that acts as a catalyst with respect to the combustion of the inflammable gas.

However, when the gas detection film is heated by the heater, the heat generated by the heater is not uniformly transferred to the gas detection film, and temperature unevenness may occur in the gas detection film. Additionally, if the distribution of catalyst particles or film thickness in the gas detection film itself is uneven, there is a possibility that the amount of generated heat caused by the combustion of the inflammable gas becomes uneven, and the temperature unevenness occurs in the gas detection film. Generally, since the activity of a combustion catalyst that combusts an inflammable gas depends strongly on temperature, if the temperature unevenness occurs and a low-temperature region is formed, the amount of catalytic combustion decrease greatly in the region. Therefore, if the temperature unevenness occurs, there is a concern that the amount of catalytic combustion of the inflammable gas in the entire gas reaction film may decrease, and the detection sensitivity of the gas may degrade.

SUMMARY OF THE INVENTION

The invention has been made in order to solve the above-described related-art problems, and an object thereof is to provide a technique of uniformizing the temperature of a gas reaction film for detecting an inflammable gas, in a catalysis combustion type gas sensor that detects the inflammable gas.

A catalysis combustion type gas sensor of the invention includes a heat-insulating portion; a heater that is formed on the heat-insulating portion; a gas reaction film that is formed on the heater on the heat-insulating portion and includes a carrier carrying a combustion catalyst for the inflammable gas; a temperature-measuring element that is formed in the vicinity of the gas reaction film on the heat-insulating portion; and a soaking portion that is formed on the heat-insulating portion and is arranged between the heat-insulating portion and the gas reaction film. Here, the soaking portion is configured so as to decentralize heat transferred to the soaking portion in the entire soaking portion.

According to this configuration, the heat generated by the heater or the gas reaction film is transferred to the soaking portion, and is decentralized in the entire soaking portion. Therefore, since the heat generated by the heater is more uniformly transferred to the gas reaction film, and the heat is transferred from a high-temperature region of the gas reaction film via a soaking portion to a low-temperature region, the temperature of the gas reaction film is uniformized.

The soaking portion may have first and second soaking portions that are separately formed, and the heater may be arranged between the first soaking portion and the second soaking portion.

The heat generated by the heater can be more uniformly decentralized by arranging the heater between the first soaking portion and the second soaking portion. Therefore, since the heat generated by the heater can be more uniformly transferred to the gas reaction film, it is possible to make the temperature of the gas reaction film more uniform.

The temperature-measuring element may have a thermocouple including first and second thermo-electric devices formed of mutually different materials, and the soaking portion may be formed of the same material as that of the first thermo-electric device.

The first thermo-electric device and the soaking portion can be simultaneously formed by forming the soaking portion of the same material as that of the first thermo-electric device. Therefore, the manufacturing process of the catalysis combustion type gas sensor can be further simplified.

The soaking portion may be formed of metal.

A wiring line or the like and the soaking portion that are formed of metal can be simultaneously formed by forming the soaking portion of metal. Therefore, the manufacturing process of the catalysis combustion type gas sensor can be further simplified.

The catalysis combustion type gas sensor may further include a compensating portion provided separately from a gas detecting portion having the heater, the gas reaction film, the temperature-measuring element, and the soaking portion. The compensating portion may include a compensating portion heater that is formed on the heat-insulating portion, and a reference film that is formed on the compensating portion heater on the heat-insulating portion and includes a carrier that does not carry the combustion catalyst for the inflammable gas, a compensating portion temperature-measuring element that is formed in the vicinity of the reference film on the heat-insulating portion, and a compensating portion soaking portion that is formed on the heat-insulating portion and is arranged between the heat-insulating portion and the reference film. The compensating portion soaking portion may be configured so as to decentralize the heat transferred to the compensating portion soaking portion in the entire compensating portion soaking portion.

Since a change in the temperature of the gas reaction film caused by an external factor can be compensated for by providing the catalysis combustion type gas sensor with the compensating portion configured similar to the gas detecting portion, the detection sensitivity of the inflammable gas can be made higher.

In addition, the invention can be realized in various aspects. For example, the invention can be realized in aspects, such as gas sensors, sensor modules using the gas sensors, combustible gas detecting devices and combustible gas detection systems using the sensor modules, leakage test devices or leakage test systems using the gas sensors, the sensor modules, and combustible gas detecting devices.

DETAILED DESCRIPTION OF THE INVENTION

A. First Embodiment

A1. Sensor Module

Figure 1A:
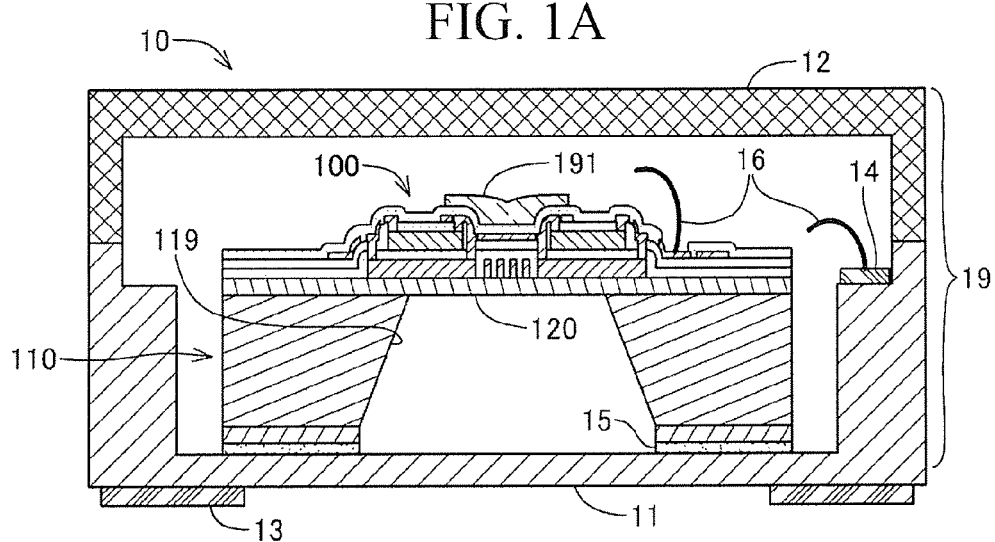
FIGS. 1A and 1B are a sectional view and a plan view showing a sensor module in a first embodiment of the invention.
Figure 1B:
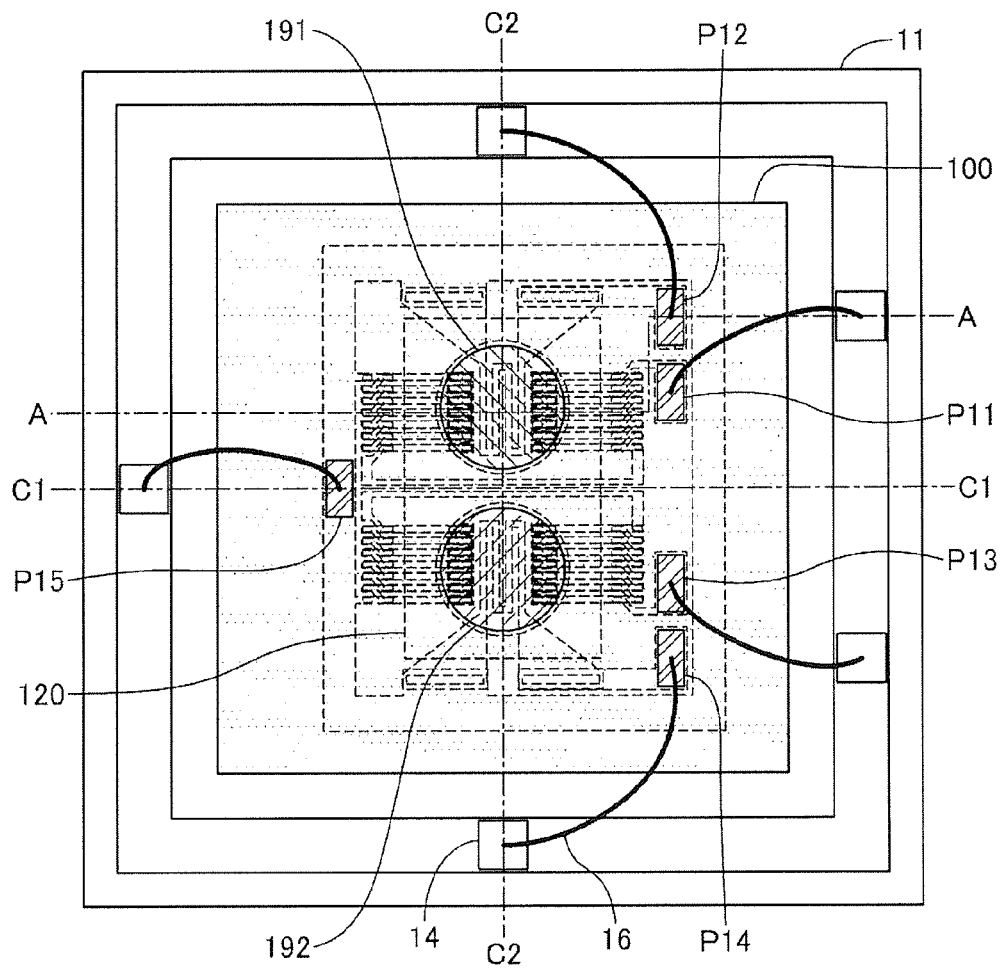

FIGS. 1A and 1B are explanatory views showing the configuration of a catalysis combustion type gas sensor module 10 (hereinafter also simply referred to as a "sensor module 10") in a first embodiment of the invention. FIG. 1A shows a section of the sensor module 10. In the sensor module 10 of the first embodiment, a sensor chip 100 is mounted within a package 19 consisting of a case 11 and a cap 12. The cap 12 is formed of, for example, a sintered metal, such as stainless steel or brass, a wire net made of stainless steel, or the like, or porous ceramics. Accordingly, the permeability inside or outside of the package 19 is secured, contamination of the sensor chip 100 is limited, and explosion proofing of the sensor module 10 itself is achieved. The sensor chip 100 is fixed to the case 11 by the substrate 110 provided with a cavity 119 being bonded to the case 11 by a die-bonding material 15.

FIG. 1B shows the sensor chip 100 fixed to the case 11 as seen from a top surface. One-dot chain line A in FIG. 1B is a cutting line showing the position of the section shown in FIG. 1A. Additionally, one-dot chain lines C1 and C2 are centerlines showing the center position of the sensor chip 100. As shown in FIG. 1B, the top surface of the sensor chip 100 is formed with bonding pads P11 to P15 from which a conductive film is exposed. Connection between the sensor chip 100 and an external circuit is possible by connecting the bonding pads P11 to P15 and a terminal 14 connected to an external electrode 13 of the case 11 with a wire 16.

A gas reaction film 191 for catalytically combusting an inflammable gas and a reference film 192 for comparison are provided on the top surface of the sensor chip 100. If an inflammable gas is transmitted through the cap 12 and reaches the sensor chip 100, in the gas reaction film 191, the inflammable gas is catalytically combusted and the heat of an amount according to the concentration of the inflammable gas is generated. Therefore, the temperature of the gas reaction film 191 rises according to the concentration of the inflammable gas. Meanwhile, the temperature rise caused by the catalytic combustion does not occur in the reference film 192. Although the details will be described below, the sensor chip 100 outputs signals showing the respective temperatures of the gas reaction film 191 and the reference film 192. The concentration of the inflammable gas in an atmosphere can be measured by obtaining a temperature difference between the gas reaction film 191 of which the temperature rises due to the catalytic combustion of the inflammable gas, and the reference film 192 without the temperature rise caused by inflammable gas, on the basis of these output signals. In addition, it can be said that the sensor chip 100 is a gas sensor itself since the sensor chip functions to detect gas, in the sensor module 10 in this way. Hence, the shaft 100 is hereinafter referred to as the second rotary shaft 100.

As shown in FIG. 1B, the gas sensor 100 is formed symmetrically with respect to the centerline C1 extending in a lateral direction, and is formed substantially symmetrically with respect to the centerline C2 extending in a longitudinal direction. Therefore, in the following, only one of the portions having a symmetric property in this way will be described as long as there is no necessity for further description. Additionally, a portion closer to the gas reaction film 191 side than the centerline C1 is configured so as to output the signal showing the temperature of the gas reaction film 191, that is, the signal according to the concentration of the inflammable gas in an atmosphere, and a portion closer to the reference film 192 side than the centerline C1 outputs a signal for compensating a change in the temperature of the gas reaction film 191 caused by an external factor. Therefore, the portion closer to the gas reaction film 191 side can also be referred to as a gas detecting portion that detects gas, and the portion closer to the reference film 192 side can also be referred to as a compensating portion that compensates an output fluctuation caused by an external factor. In this way, since the gas detecting portion and the compensating portion are substantially symmetrically formed, the gas sensor 100 can compensate the fluctuation of output caused by an external factor, such as a change in environmental temperature, with high precision.

A2. Manufacturing Process of Gas Sensor

As shown in FIG. 1A, the gas sensor 100 has a substrate 110 provided with the cavity 119, and an insulating film 120 formed on a top surface of the substrate 110. A plurality of films (functional film) that form the structure (to be described below) for realizing the detection function of gas are laminated on the insulating film 120. Specifically, various functional films are formed on the insulating film 120 by forming semiconductors, conductors, insulators, and the like as films and performing patterning if necessary. In addition, since these functional films can be formed using techniques that are well known as methods for manufacturing semiconductor devices, specific formation methods of the respective functional films will be omitted. Additionally, the insulating film 120 and the functional films laminated on the insulating film 120 will be appropriately added or omitted with changes in the manufacturing process or the structure of the gas sensor.

Figure 2A:
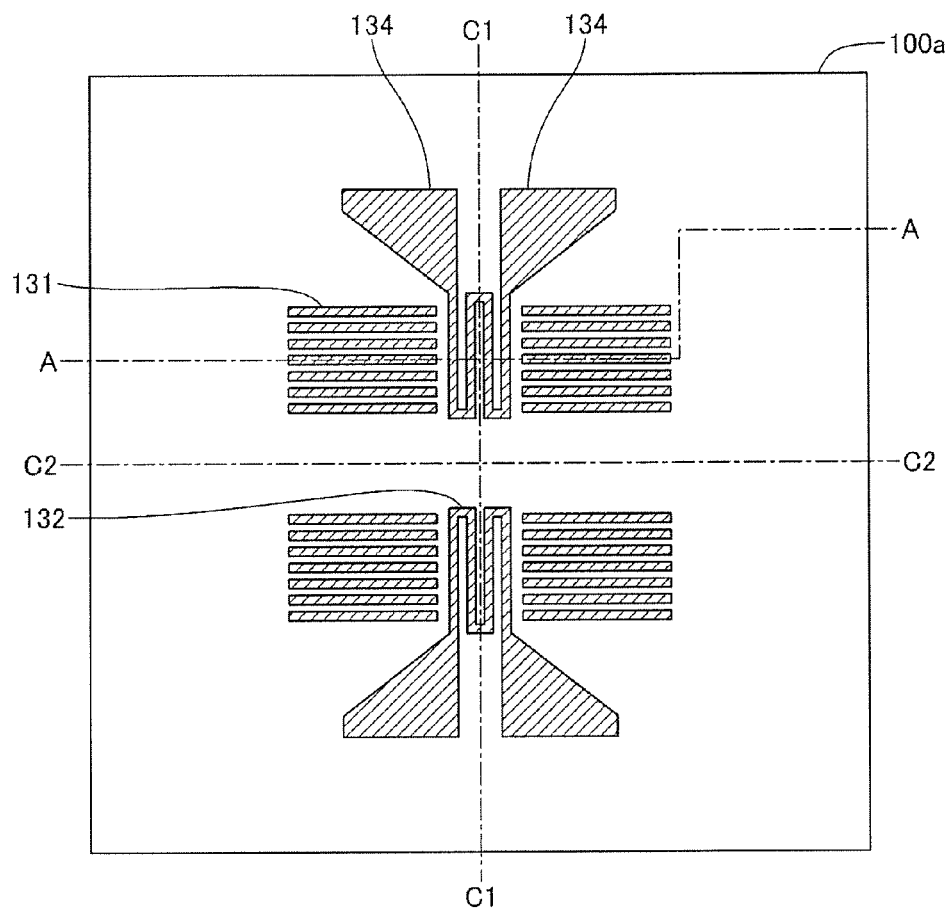
FIGS. 2A and 2B are a plan view and a sectional view showing an intermediate product of the gas sensor of the first embodiment manufactured in an intermediate step of a manufacturing process.
Figure 2B:
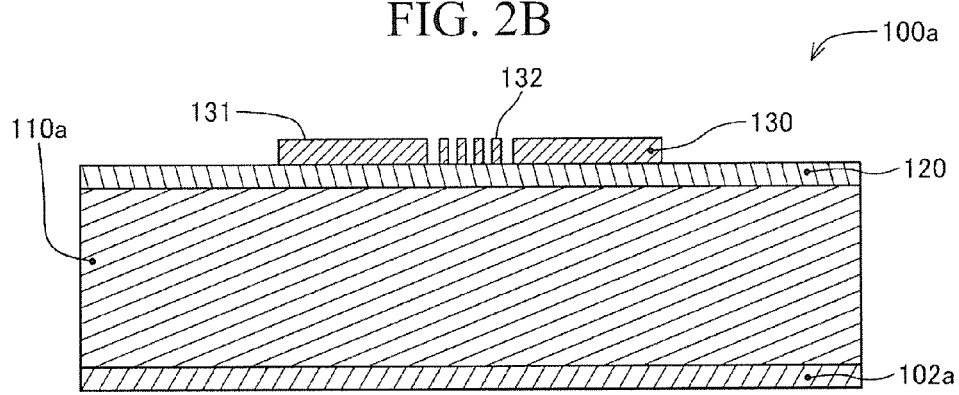

FIGS. 2A and 2B are explanatory views showing the shape of an intermediate product (intermediate body) 100a in an intermediate step of a manufacturing process of the gas sensor 100. FIG. 2A shows that an intermediate product 100a is seen from a top surface, and FIG. 2B shows a section of the intermediate product 100a in a cutting line A of FIG. 2A. In the manufacturing process of the gas sensor 100, first, a substrate 110a, such as silicon (Si), which does not have the cavity 119 (FIG. 1A), is prepared. Next, the insulating film 120 is formed on the top surface of the prepared substrate 110a by forming films of oxidization silicon ($SiO_2$), silicon nitride ($Si_3N_4$), and $SiO_2$ in this order. In addition, the insulating film 120 is not the multilayer film of SiO2 and $Si_3N_4$, and can also be a single layer film of silicon oxynitride (SiON). Additionally, a mask film 102a is formed on a back surface of the substrate 110a by forming films of $SiO_2$ and $Si_3N_4$ in this order.

An n-type semiconductor film 130 is formed by forming an n-type polysilicon film on the insulating film 120 formed on the substrate 110a after the insulating film 120 and the mask film 102a are formed on the substrate 110a. The intermediate product 100a in which an n-type thermo-electric device 131, a heater 132, and heater wiring lines 133 and 134 for energizing the heater 132 are formed on the insulating film 120 is obtained by patterning the n-type semiconductor film 130.

Figure 3A:
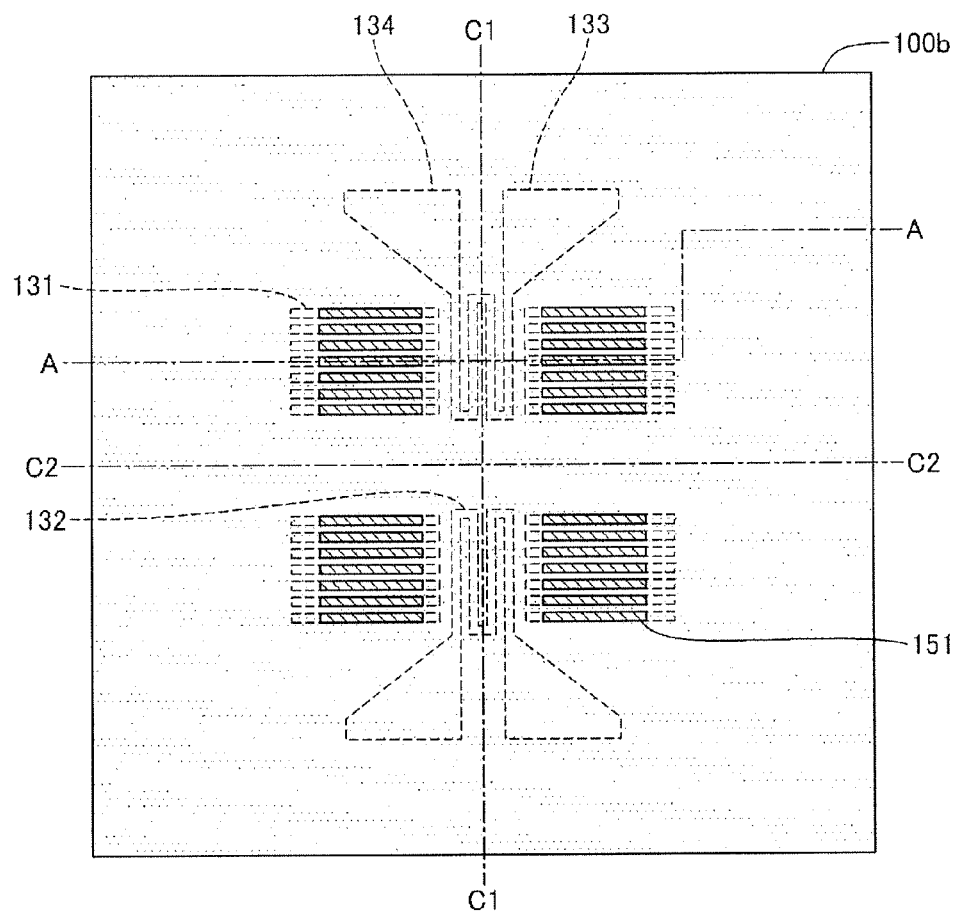
FIGS. 3A and 3B are a plan view and a sectional view showing the intermediate product of the gas sensor of the first embodiment manufactured in a process after the manufacturing process shown in FIGS. 2A and 2B.
Figure 3B:
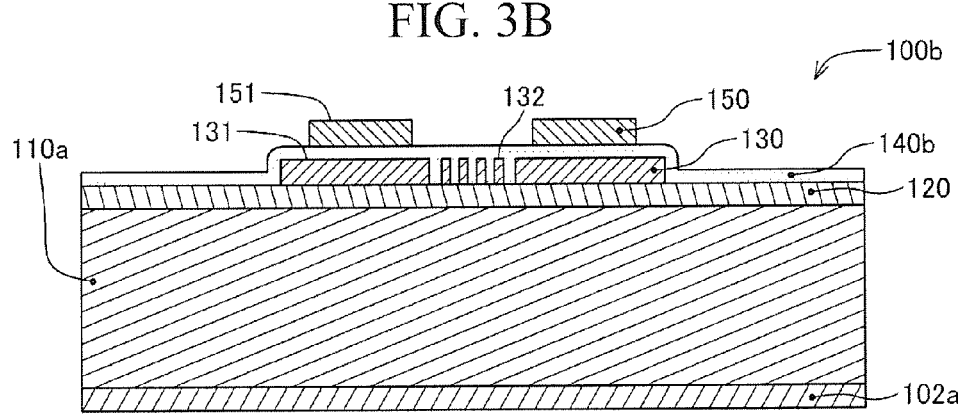

FIGS. 3A and 3B are explanatory views showing the shape of an intermediate product (intermediate body) 100b in a step after the process shown in FIGS. 2A and 2B. FIG. 3A shows the intermediate product 100b as seen from a top surface, and FIG. 3B shows a section of the intermediate product 100b in the cutting line A of FIG. 3A. A first interlayer insulating film 140b is formed by forming a $SiO_2$ film on the intermediate product 100a after the formation (FIGS. 2A and 2B) of the n-type semiconductor film 130. Next, a p-type semiconductor film 150 is formed by forming a p-type polysilicon film on the first interlayer insulating film 140b. The intermediate product 100b in which a p-type thermo-electric device 151 is formed on the first interlayer insulating film 140b is obtained by patterning the p-type semiconductor film 150.

In addition, as materials for at least one of the n-type semiconductor film 130 and the p-type semiconductor film 150, various semiconductors of iron silicide ($FeSi_2$), silicon germanium (SiGe), bismuth antimony (BiSb) or the like instead of polysilicon may be used. Additionally, in the first embodiment, the n-type semiconductor film 130 is formed on the insulating film 120, and the p-type semiconductor film 150 is formed on the first interlayer insulating film 140b. However, it is also possible to reverse the dope types of these semiconductor films. Moreover, it is also possible to replace at least one of the two semiconductor films 130 and 150 with a conductive film made of metal. It should be noted herein that, when both of the two semiconductor films 130 and 150 are replaced with conductive films, the two conductive films are formed of different metal materials.

Figure 4A:
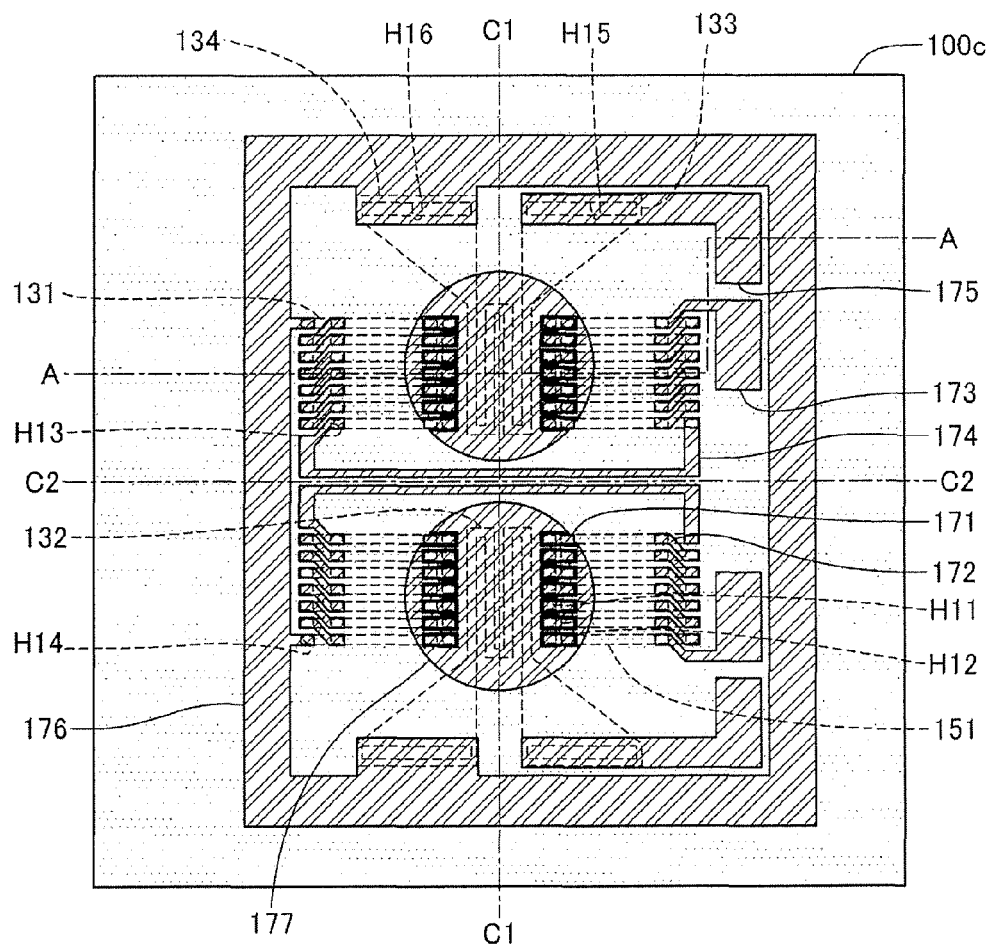
FIGS. 4A and 4B are a plan view and a sectional view showing the intermediate product of the gas sensor of the first embodiment manufactured in the process after the manufacturing process shown in FIGS. 3A and 3B.
Figure 4B:
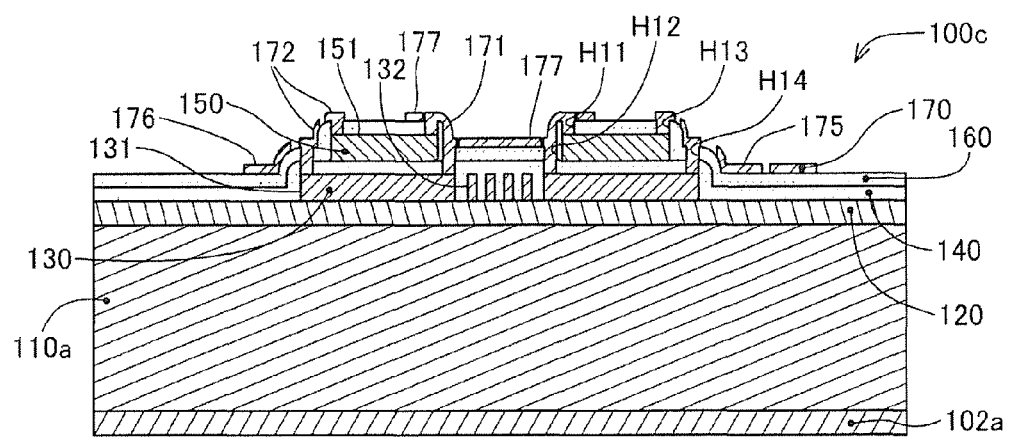

FIGS. 4A and 4B are explanatory views showing the shape of an intermediate product (intermediate body) 100c in a step after the process shown in FIGS. 3A and 3B. FIG. 4A shows the intermediate product 100c as seen from a top surface, and FIG. 4B shows a section of the intermediate product 100c in the cutting line A of FIG. 4A. $SiO_2$ is formed as a film on the intermediate product 100b to form a second interlayer insulating film (not shown) after the formation (FIGS. 3A and 3B) of the p-type semiconductor film 150. Then, the first interlayer insulating film 140b and the second interlayer insulating film are patterned altogether. Accordingly, first and second interlayer insulating films 140 and 160 provided with openings (contact holes) H11 to H16 are formed. The n-type semiconductor film 130 is exposed in the contact holes H12, H14, H15, and H16, and the p-type semiconductor film 150 is exposed in the contact holes H11 and H13.

After the formation of the first and second interlayer insulating films 140 and 160, film formation and patterning of platinum (Pt) are performed and a conductive film 170 is formed. Accordingly, the intermediate product 100c formed with the conductive film 170 is obtained. In addition, as materials for forming the conductive film 170, various kinds of metal including alloys, such as tungsten (W), tantalum (Ta), gold (Au), aluminum (Al), or Al alloys, instead of Pt, may be used. Additionally, an adhesion layer made of titanium (Ti) or chromium (Cr) may be formed on at least one surface of the conductive film 170.

As described above, the first and second interlayer insulating films 140 and 160 are provided with the contact holes H11 to H16 from which the semiconductor films 130 and 150 are exposed. Therefore, wiring lines and electrodes that connect the n-type semiconductor film 130, the p-type semiconductor film 150, and the conductive film 170 so as to realize predetermined functions are formed by forming the conductive film 170. Specifically, a hot junction connection line 171, a cold junction connection line 172, a signal output electrode 173, a thermopile connection line 174, a heater energization electrode 175, and a ground wiring line 176 are formed as the conductive film 170. Additionally, simultaneously with these wiring lines and electrodes, a soaking film 177 is formed in the vicinity of the hot junction connection line 171.

The hot junction connection line 171 forms a hot junction for connecting the n-type thermo-electric device 131 and the p-type thermo-electric device 151, which are vertically laminated, to measure the temperature of the gas reaction film 191 or the reference film 192 (FIGS. 1A and 1B). The cold junction connection line 172 connects the n-type thermo-electric device 131 and the p-type thermo-electric device 151 adjacent to each other so as to form a cold junction serving as a reference for temperature measurement, and serially connects a plurality of thermocouples consisting of the n-type thermo-electric device 131 and the p-type thermo-electric device 151. The thermopile connection line 174 further serially connects thermopiles that serially connect the thermocouples. The signal output electrode 173 is connected to the p-type thermo-electric device 151 at one end of the thermopiles that are serially connected. Meanwhile, the n-type thermo-electric device 131 at the other end of the thermopiles that are serially connected is connected to the ground wiring line 176. Accordingly, a voltage corresponding to a temperature difference between the hot junction and the cold junction is generated in the signal output electrode 173 with respect to the ground wiring line 176. Since the two heater wiring lines 133 and 134 connected to the heater 132 are respectively connected to the heater energization electrode 175 and the ground wiring line 176, the heater 132 can be energized by applying a voltage between the heater energization electrode 175 and the ground wiring line 176. In addition, in this way, since the hot junction formed by the hot junction connection line 171 has a function of measuring the temperature of the gas reaction film 191 or the reference film 192, this hot junction can also be referred to as a temperature-measuring element.

Figure 5A:
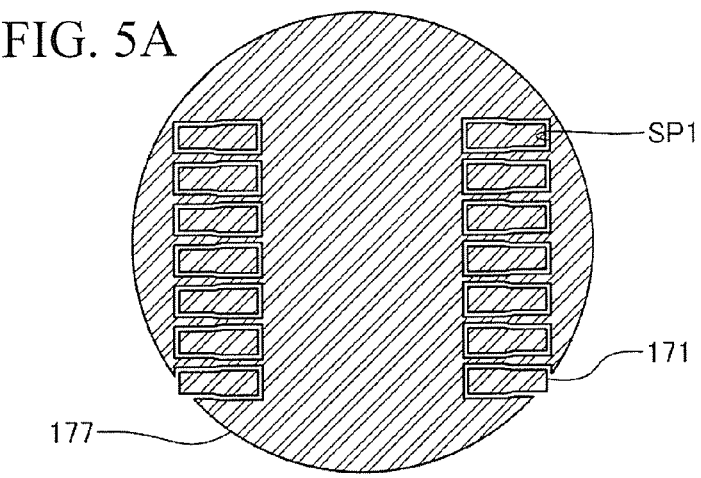
FIGS. 5A, 5B, and 5C are plan views showing examples of formation patterns of soaking films formed on the intermediate product of the gas sensor of the first embodiment shown in FIGS. 4A and 4B.
Figure 5B:
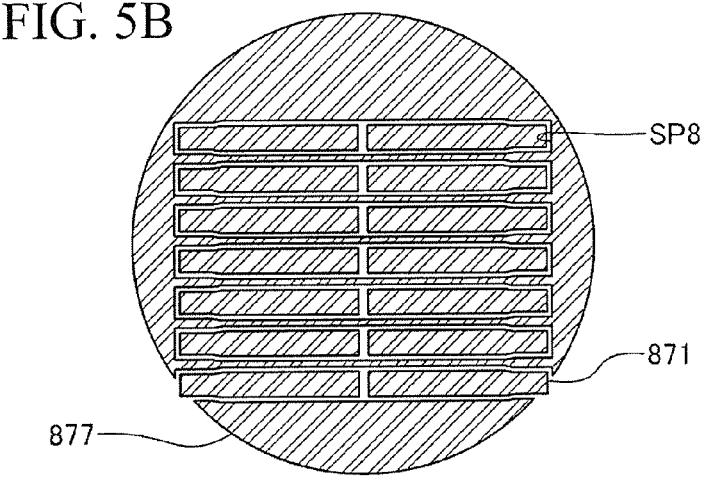
Figure 5C:
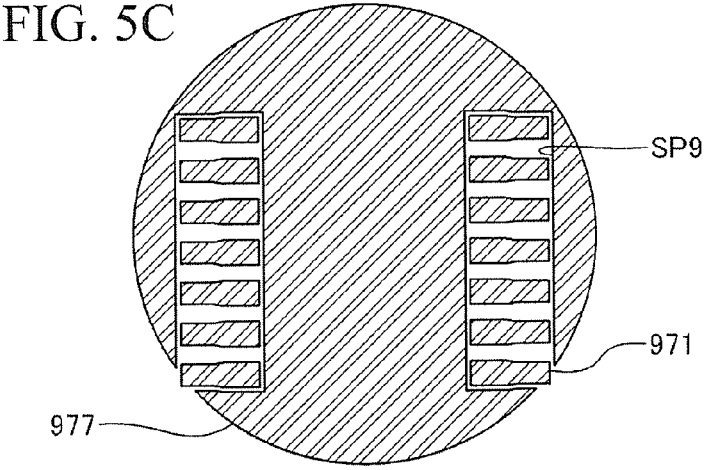

FIGS. 5A, 5B, and 5C are explanatory views showing examples of formation patterns of soaking films. FIG. 5A shows a formation pattern of the soaking film 177 in the first embodiment and the hot junction connection line 171 formed in the vicinity of the soaking film 177, and FIGS. 5B and 5C show modification examples of formation patterns of soaking films 877 and 977 and hot junction connection lines 871 and 971 formed in the vicinity of the soaking films 877 and 977. As shown in FIG. 5A, the soaking film 177 of the first embodiment is formed so as to form a narrow gap SP1 between the soaking film and the hot junction connection lines 171. Since the gap SP1 is narrow in this way, heat is excellently transferred between the soaking film 177 and the hot junction connection line 171. Both of the soaking film 177 and the hot junction connection line 171 are formed as the conductive film 170 with high thermal conductivity. Therefore, in a region including the soaking film 177 and the hot junction connection line 171, heat is decentralized in the entire region and temperature is uniformized. In this way, since the soaking film 177 and the hot junction connection line 171 decentralize heat and uniformize the temperature of the region including the soaking film 177 and the hot junction connection line 171, these can also be altogether referred to as a "soaking portion".

In the example of FIG. 5B, since the hot junction connection line 871 extends in a central direction of the soaking film 877, the conductive film is not continuous in most of the region including the soaking film 877 and the hot junction connection line 871. However, since a gap SP8 between the soaking film 877 and the hot junction connection line 871 is narrow even in the case of FIG. 5B, the transfer of heat between the soaking film 877 and the hot junction connection line 871 can be made excellent. Therefore, in the region where the hot junction connection line 871 is formed, heat is transferred via the soaking film 877. Thus, in the region including the soaking film 877 and the hot junction connection line 871, heat is decentralized in the entire region and temperature is uniformized.

In the example of FIG. 5C, the soaking film 977 is not formed between the hot junction connection lines 971 adjacent to each other. Therefore, heat is not excellently transferred between the hot junction connection lines 971 adjacent to each other. However, even in the case of FIG. 5C, the soaking film 977 is continuous in an adjoining direction of the hot junction connection lines 971, and a gap SP9 between the soaking film 977 and the hot junction connection line 971 is narrow in a direction orthogonal to the adjoining direction. Therefore, heat is sufficiently and excellently transferred via the soaking film 977 between the hot junction connection lines 971 adjacent to each other. Thus, in the region including the soaking film 977 and the hot junction connection line 971, heat is decentralized in the entire region and temperature is uniformized.

Figure 6A:
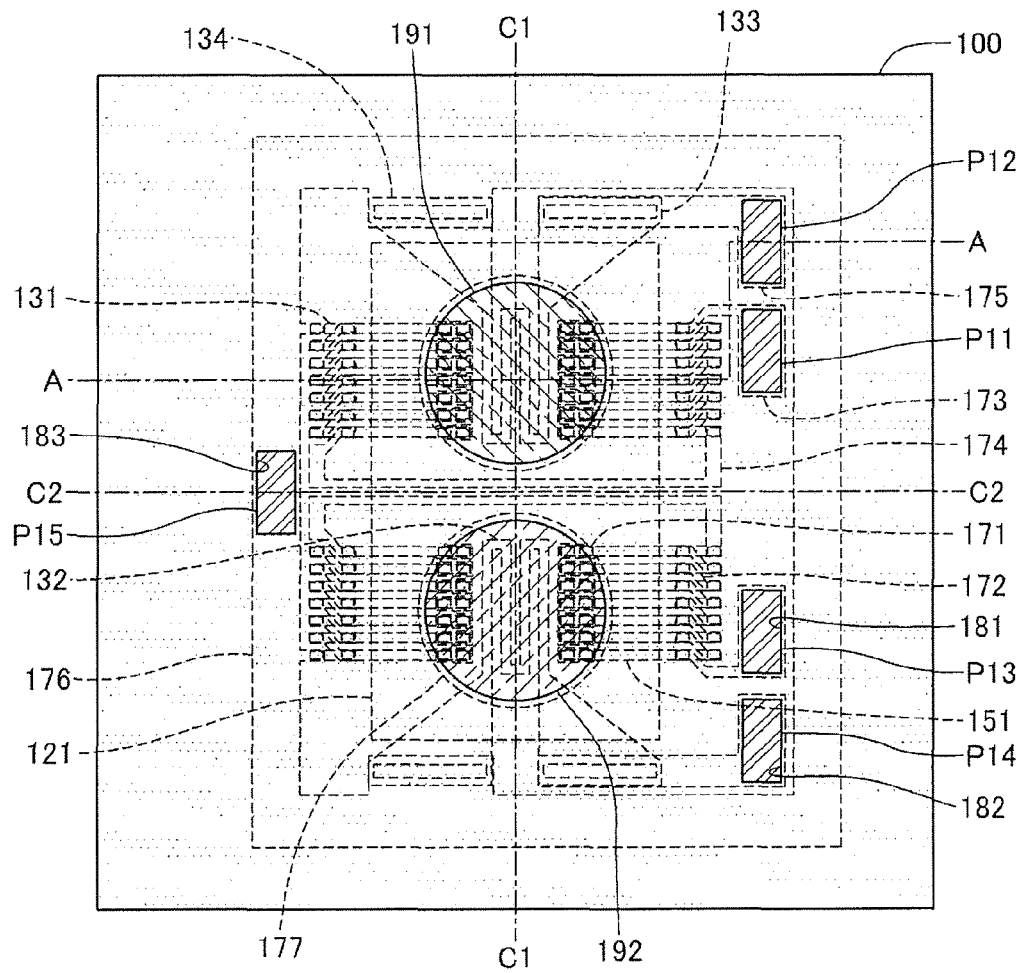
FIGS. 6A and 6B are a plan view and a sectional view showing the gas sensor of the first embodiment manufactured in a process after the manufacturing process shown in FIGS. 4A and 4B.
Figure 6B:
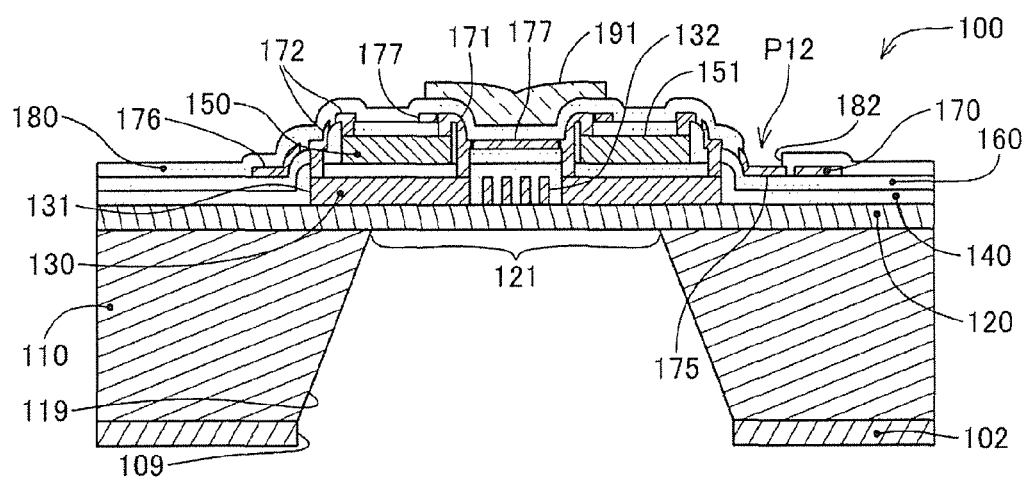

FIGS. 6A and 6B are explanatory views showing the shape of the gas sensor 100 obtained by further advancing a process after the step shown in FIGS. 4A and 4B. FIG. 6A shows that the gas sensor 100 is seen from a top surface, and FIG. 6B shows a section of the gas sensor 100 in the cutting line A of FIG. 6A. After the formation (FIGS. 4A and 4B) of the conductive film 170, $SiO_2$ is formed as a film on the intermediate product 100c to form a protective film 180. Bonding pads (signal output pads) P11 and P13 from which the signal output electrode 173 is exposed, bonding pads (heater energization pads) P12 and P14 from which the heater energization electrode 175 is exposed, and a bonding pad (ground pad) P15 from which the ground wiring line 176 is exposed are formed by providing openings 181 to 183 through the patterning of the protective film 180.

The cavity 119 provided in the substrate 110 is formed after the protective film 180 is formed. When forming the cavity 119, first, an opening 109 is formed in the mask film 102a. Next, the cavity 119 is formed by etching the substrate 110a by using the mask film 102 provided with the opening 109 as a mask. The etching can be performed, for example, by crystalline anisotropy etching using a solution of tetramethyl ammonium hydroxide (TMAH) or potassium hydroxide (KOH). Additionally, the cavity 119 may be formed by dry etching, such as a so-called Bosch process, in addition to wet etching. A membrane 121 in which the insulating film 120 is exposed on a back side is formed by forming the cavity 119 in this way. In addition, as can be seen from FIGS. 6A and 6B, the membrane 121 is formed so as to cross the cavity 119.

In addition, in the example of FIGS. 6A and 6B, the cavity 119 is formed by etching a substrate from a bottom surface side. However, the cavity can also be formed by etching a substrate from a top surface side. In this case, the cavity can be formed by providing through-holes in the insulating film 120, the first and second interlayer insulating films 140 and 160, and the protective film 180 and etching the substrate through the through-holes. When the substrate is etched from the top surface side in this way, the gas sensor can be manufactured only by the processing of the substrate from the top surface side, and a residual portion of the substrate can be made larger than that in a case where etching is performed from the bottom surface side. Therefore, it is preferable to etch the substrate from the top surface side so that it is possible to simplify the manufacturing process of the gas sensor to make the yield higher, and the strength of the substrate after the etching can be made higher. Meanwhile, if the substrate is etched from the bottom surface side, the cavity 119 can be formed without providing the through-hole in the insulating film 120. Thus, it is preferable to etch the substrate from the bottom surface side so that formation of the through-holes in the membrane and degradation of strength can be limited, and damage of the membrane can be limited.

Additionally, the cavity is not necessarily formed in the substrate. For example, it is also possible to form the cavity between the substrate and the insulating film or between the insulating film 120, and the n-type semiconductor film and the first interlayer insulating film. Such a cavity in the substrate can be formed by forming the respective functional films including the protective film as described above after a sacrifice film is formed in a region in the substrate or the insulating film 120 where the cavity is formed then by providing the through-holes that lead from the protective film top surface to the sacrifice film and removing the sacrifice film through the through-holes. Resins, such as polyimide, or semiconductors, such as polysilicon, can be used as materials for forming the sacrifice film. The sacrifice film made of resin can be removed by etching, and the sacrifice film made of a semiconductor can be removed by ashing. It is noted herein that, when a semiconductor is used as the sacrifice film, in order to prevent etching of the substrate or the n-type semiconductor film, a prevention film made of $SiO_2$, $Si_3N_4$, or the like is formed on the substrate or the insulating film 120 and the sacrifice film. When the cavity is formed in the substrate in this way, the strength of the substrate can be made higher than that in a case where a substrate is etched. Meanwhile, it is preferable to etch the substrate so that the manufacturing process of the gas sensor can be further simplified.

The gas reaction film 191 and the reference film 192 are formed on the protective film 180 after the formation of the cavity 119. Specifically, the regions where the gas reaction film 191 and the reference film 192 are formed are respectively coated with paste including alumina particles that are made to carry Pt particulates as a combustion catalyst and paste including alumina particles that are not made to carry the catalyst. The coating of the paste can be performed using a coating technique using a dispenser or a screen printing technique. The gas reaction film 191 and the reference film 192 are formed by baking after being coated with paste. The gas sensor 100 is obtained by forming the gas reaction film 191 and the reference film 192 on the protective film 180 in this way.

In addition, it is also possible to use palladium (Pd) particulates as the combustion catalyst used for the gas reaction film 191 instead of the Pt particulates. Additionally, in order to bring the specific heat of the reference film 192 close to that of the gas reaction film 191, metal oxide, such as copper oxide (CuO), may be mixed with the paste for forming the reference film 192. Moreover, as a carrier included in the reference film 192, a carrier that carries the combustion catalyst (for example, ultrafine particles of Au) that selectively acts on a specific gas as a catalyst may be used. Even in this case, regarding inflammable gases other than the specific gas, it can be said that the combustion catalyst is not carried in the carrier of the reference film 192.

As shown in FIGS. 6A and 6B, in the gas sensor 100 of the first embodiment, all of the hot junction connection line 171 that forms the hot junction, the soaking film 177, the gas reaction film 191 and the reference film 192, and the heater 132 are formed on the membrane 121. Meanwhile, the cold junction connection line 172 that forms the cold junction is formed in a region (substrate region) where the substrate 110 remains. Additionally, in the gas sensor 100, the hot junction connection line 171 and the soaking film 177 that are the soaking portion are arranged between the heater 132, and the gas reaction film 191 and the reference film 192. Also, the gas reaction film 191 and the reference film 192 are formed to be smaller than the soaking portion so as to fit inside the soaking portion.

Additionally, the hot junction formed by the hot junction connection line 171 is formed under the gas reaction film 191 or the reference film 192, and the cold junction formed by the cold junction connection line 172 is formed on a substrate region where the cavity 119 is not formed. It is noted herein that the hot junction is not necessarily formed under the gas reaction film 191 or the reference film 192. Generally, the hot junction only has to be formed in the vicinity of the gas reaction film 191 or the reference film 192. Even in this way, the temperature of the gas reaction film 191 or the reference film 192 can be measured.

A3. Operation of Gas Sensor

As shown in FIGS. 6A and 6B, since the hot junction connection line 171 is formed under each of the gas reaction film 191 and the reference film 192, the temperature of the hot junction connection line 171 becomes approximately equal to the temperature of the gas reaction film 191 or the reference film 192. Meanwhile, as shown in FIGS. 1A and 1B, the substrate 110 is bonded to the case 11 of the package 19 by the die-bonding material 15. Thus, the temperature of the cold junction connection line 172 arranged in the substrate region becomes approximately equal to the temperature or environmental temperature of the package 19. Therefore, voltages corresponding to the temperatures of the gas reaction film 191 and the reference film 192 based on the environmental temperature are respectively output to the signal output pads P11 and P13. Then, the temperature difference between the gas reaction film 191 and the reference film 192 can be measured by taking a difference between the output voltages of the two signal output pads P11 and P13 to compensate for external factors, such as the environmental temperature.

When the gas sensor 100 is made to operate, a voltage is applied to between the ground pad P15 and the heater energization pads P12, and P14, and a heater 132 is caused to generate heat to raise the temperatures of the gas reaction film 191 and the reference film 192. In the gas reaction film 191, the combustion catalyst is activated as the temperature rises. Accordingly, when an inflammable gas is present in the atmosphere, the inflammable gas is catalytically combusted to generate heat, and the temperature rises according to the concentration of the inflammable gas. Meanwhile, the reference film 192 does not generate heat even when the inflammable gas is present in the atmosphere. Therefore, a temperature difference according to the concentration of the inflammable gas occurs in the gas reaction film 191 and the reference film 192. The concentration of the inflammable gas in the atmosphere can be measured by measuring the temperature difference between the gas reaction film 191 and the reference film 192 as described above.

If the heat generated by the heater 132 is uniformly transferred to neither the gas reaction film 191 nor the reference film 192 when the temperatures of the gas reaction film 191 and the reference film 192 are raised with the heat generated by the heater 132, temperature unevenness occurs in the gas reaction film 191 or the reference film 192. Additionally, in the gas reaction film 191, if the distribution of the catalyst particles or film thickness becomes uneven, the amount of generated heat caused by the combustion of the inflammable gas becomes uneven, and temperature unevenness occurs in the gas reaction film 191.

If the temperature unevenness occurs in the gas reaction film 191 or the reference film 192, the symmetric property of the temperature distribution in the membrane 121 collapses, and compensation of the external factors using the compensating portion having the reference film 192 cannot be sufficiently performed with high precision. Therefore, the difference (offset) between the two signal output pads P11 in case there is no inflammable gas, and the voltage of P13 may increase, or the change (drift) of offset caused by the environmental temperature, a gas flow rate, or the like may increase. If the offset or the drift increase, there is a concern that detection of a low-concentration gas becomes difficult and the measurement reproducibility of the gas concentration may degrade.

Moreover, since the activity of the combustion catalyst that the gas reaction film 191 has changes within the gas reaction film 191 if the temperature unevenness occurs in the gas reaction film 191, the detection sensitivity of the inflammable gas is influenced. Specifically, since the activity of the combustion catalyst decreases rapidly with a drop in temperature, a region with a low temperature is generated. Accordingly, the amount of catalytic combustion of the inflammable gas in the entire gas reaction film 191 decreases, and the detection sensitivity of the gas degrades. Additionally, even in a case where the combustion catalyst that selectively acts as the catalyst regarding a specific gas is used, if the temperature of the catalyst rises excessively in the region with a high temperature, this combustion catalyst also acts as a combustion catalyst for inflammable gases other than the specific gas, and the selectivity of a detected gas degrades.

In the gas sensor 100 of the first embodiment, the soaking portion with high thermal conductivity (that is, the soaking film 177 and the hot junction connection line 171) is arranged between the heater 132, and the gas reaction film 191 and the reference film 192. Therefore, since the heat generated by the heater 132 is uniformly transferred to each of the gas reaction film 191 and the reference film 192 after being decentralized in the entire soaking portion in the soaking portion, temperature unevenness in the gas reaction film 191 and the reference film 192 is limited. Additionally, the heat generated by the catalytic combustion in the gas reaction film 191 is also decentralized in the soaking portion. Therefore, even when the amount of generated heat caused by the combustion of the inflammable gas becomes uneven in the gas reaction film 191, temperature unevenness occurring in the gas reaction film 191 can be limited.

In this way, according to the gas sensor 100 of the first embodiment, an increase in offset or the increase in drift caused by temperature unevenness in the gas reaction film 191 and the reference film 192 is limited. Thus, it is possible to detect the inflammable gas with higher sensitivity, and the measurement reproducibility of the gas concentration can be made high. Additionally, the degradation of the detection sensitivity of the inflammable gas and the degradation of the selectivity can be limited by limiting the temperature unevenness in the gas reaction film 191.

Moreover, in the first embodiment, the soaking portion is formed of metal. Therefore, the soaking portion can be formed simultaneously with the wiring lines of the respective portions of the gas sensor 100 formed of metal (conductor). Therefore, since it becomes unnecessary to separately provide the processes for forming the soaking portion, the manufacturing process of the gas sensor 100 having the soaking portion can be further simplified. Additionally, generally, the conductive film 170 made of metal has higher toughness than the membrane 121. Thus, damage of the gas sensor 100 after the manufacturing process or completion is limited by providing the soaking portion.

In addition, since the hot junction connection line 171 that forms the hot junction and the soaking film 177 that determines most of the outer shape of the soaking portion (that is, the hot junction connection line 171 and the soaking film 177) are formed by patterning techniques used in semiconductor manufacturing processes, such as photolithography, the precision of the position of the hot junction with respect to the soaking portion can be made high. Since the heat generated in the gas reaction film 191 is transferred to the hot junction after being decentralized in the soaking portion, even when a variation is at the formation position of the gas reaction film 191, a variation in the heat transferred to each of a plurality of the hot junctions is limited. Therefore, it is possible to prevent the properties of the gas sensors 100, such as offset, drift, or sensitivity, from varying individually.

Additionally, in the gas sensor 100 of the first embodiment, as described above, all of the hot junction connection line 171 that forms the hot junction, the soaking film 177, the gas reaction film 191 and the reference film 192, and the heater 132 are formed on the membrane 121. Since the membrane 121 is generally formed to be thin (about 1 μm to 5 μm), the heat capacity of the membrane 121 itself is small. Additionally, the cavity 119 that does not transfer heat is formed in a bottom surface of the membrane 121. By forming the gas reaction film 191 in an upper part of the membrane 121 with low heat capacity formed on the cavity 191 in this way, the temperature of the gas reaction film 191 can be sufficiently raised even when there is little quantity of heat generated by the catalytic combustion of the inflammable gas in the gas reaction film 191. Therefore, the detection sensitivity of the inflammable gas in the gas sensor 100 can be made higher. In addition, since the cavity 119 formed in the bottom surface of the membrane 121 does not transfer heat, the cavity can also be said to be a heat-insulating portion.

B. Second Embodiment

FIGS. 7A and 7B, FIGS. 8A and 8B, FIGS. 9A and 9B, and FIGS. 10A and 10B are explanatory views showing respective steps of a manufacturing process of a gas sensor 200 in a second embodiment. FIGS. 7A, 8A, 9A, and 10A show that intermediate products 200a, 200b, and 200c, which that are obtained in the respective steps, and the gas sensor 200 as seen from a top surface. Additionally, FIGS. 7B, 8B, 9B, and 10B show sections of the intermediate products 200a, 200b, and 200c and the gas sensor 200 in the cutting line A. The gas sensor 200 of the second embodiment is different from the first embodiment in which the heater 132 formed as the n-type semiconductor film 130 in the first embodiment is formed as a conductive film 270, a soaking film 235 formed as an n-type semiconductor film 230 is used in addition to the soaking films MS1 to MS3 formed as the conductive film 270, and the shapes of respective portions are changed in accordance with these changes. The other points are the same as those of the first embodiment.

Figure 7A:
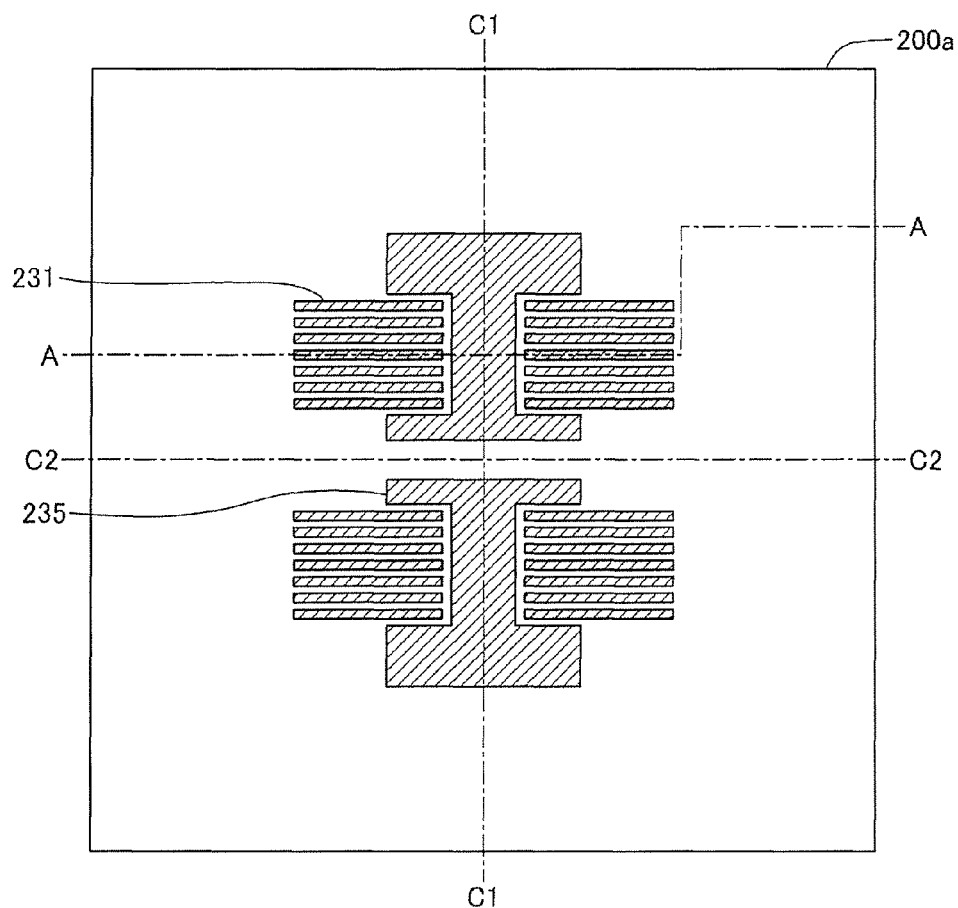
FIGS. 7A and 7B are a plan view and a sectional view showing an intermediate product of a gas sensor of a second embodiment of the invention manufactured in an intermediate step of a manufacturing process.
Figure 7B:
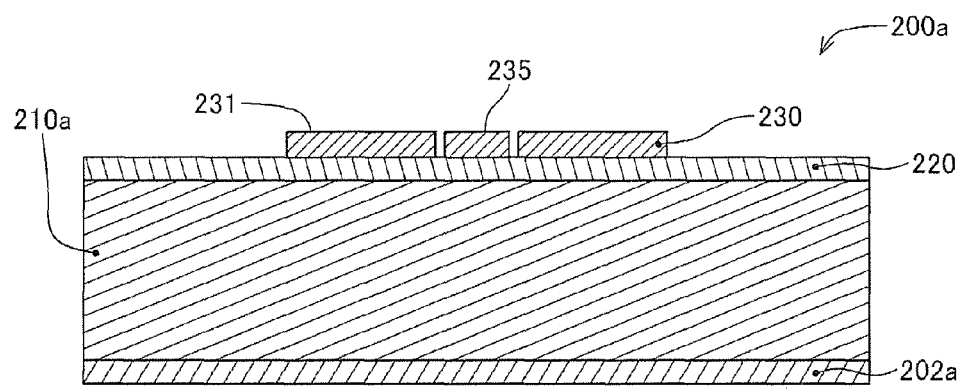
Figure 8A:
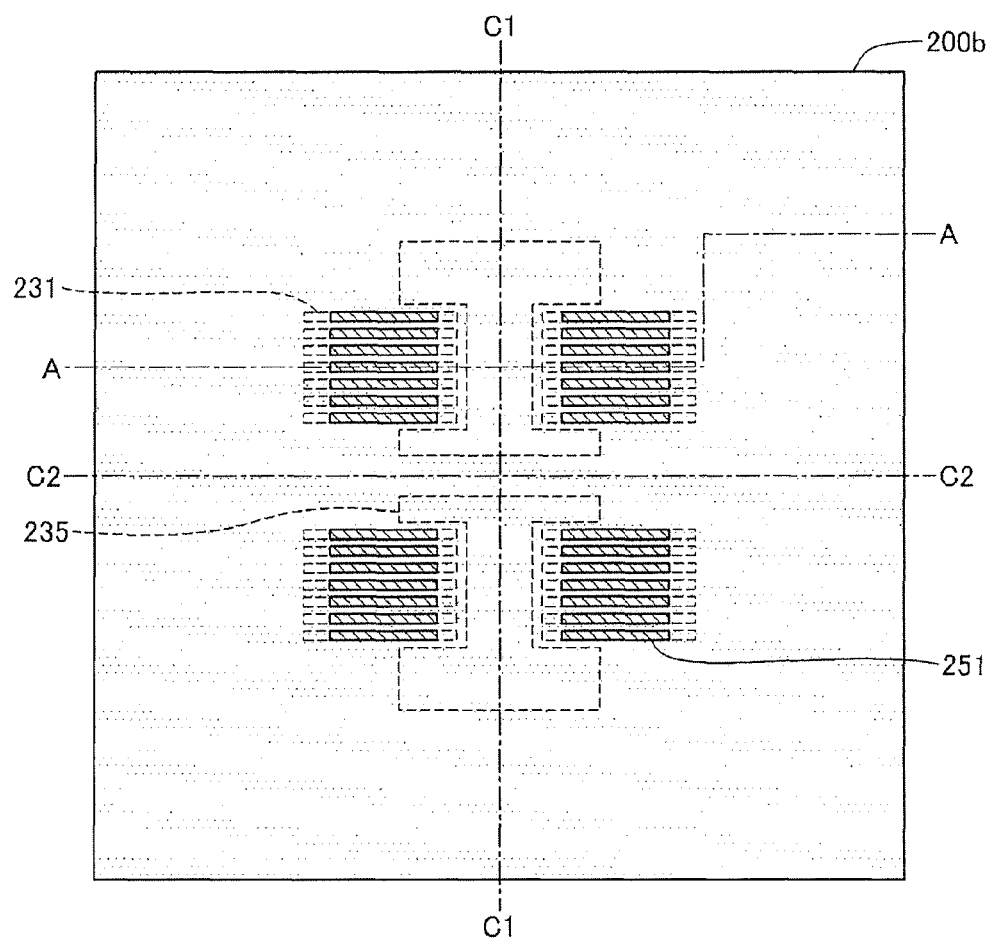
FIGS. 8A and 8B are a plan view and a sectional view showing the intermediate product of the gas sensor of the second embodiment manufactured in a process after the manufacturing process shown in FIGS. 7A and 7B.
Figure 8B:
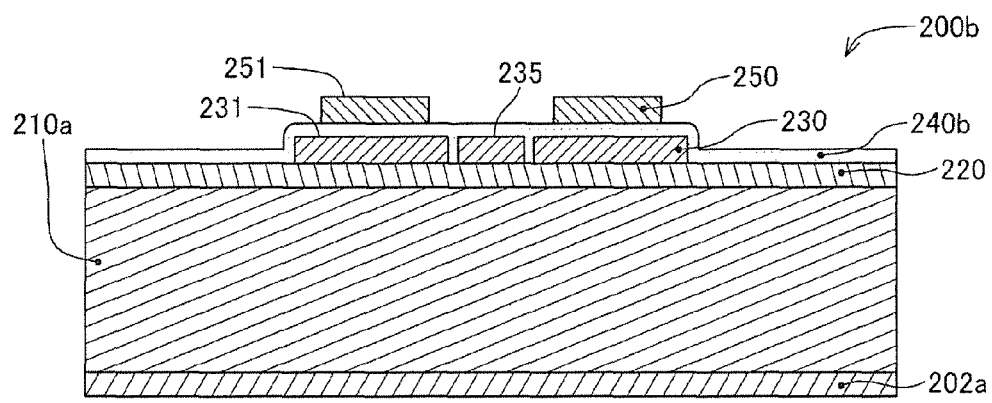
Figure 9A:
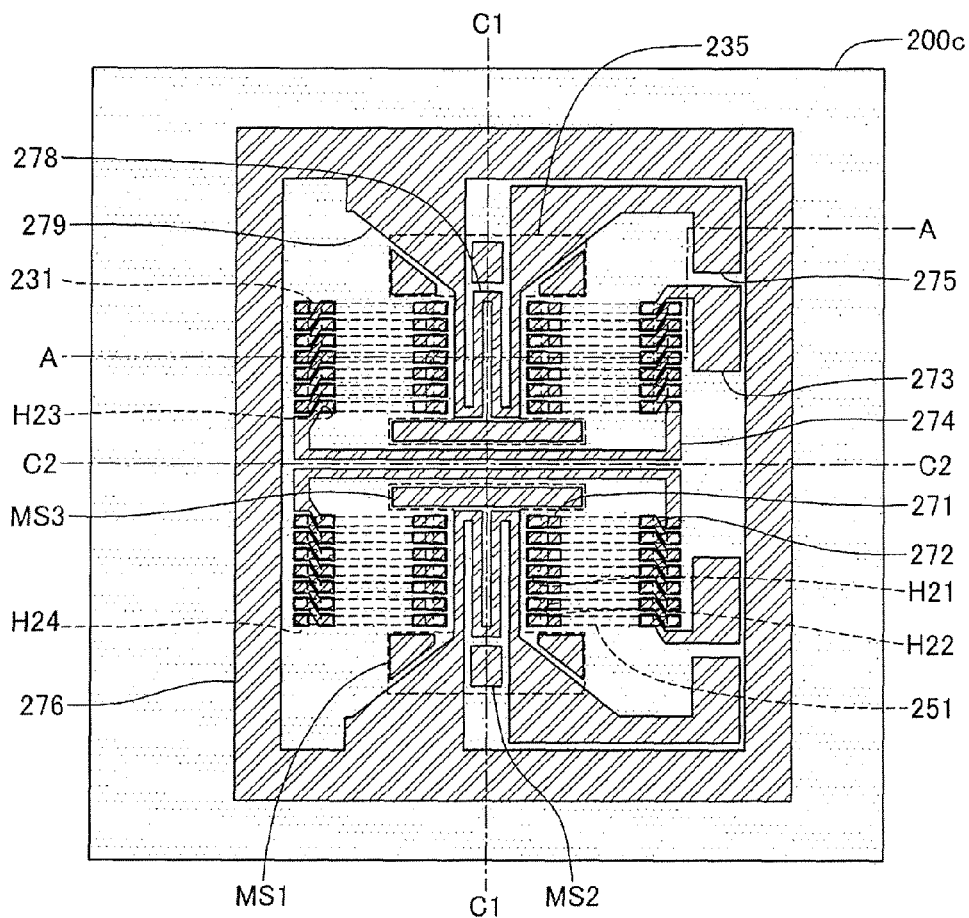
FIGS. 9A and 9B are a plan view and a sectional view showing the intermediate product of the gas sensor of the second embodiment manufactured in a process after the manufacturing process shown in FIGS. 8A and 8B.
Figure 9B:
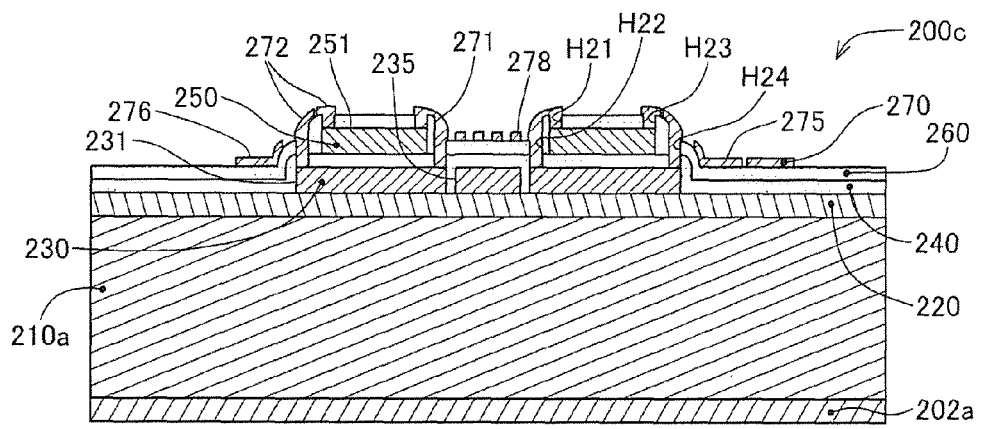

Similar to the first embodiment, in the manufacturing process of the gas sensor 200, first, as shown in FIGS. 7A and 7B, a substrate 210a on which an insulating film 220 and a mask film 202a are formed is prepared, and the n-type semiconductor film 230 having an n-type thermo-electric device 231 and the soaking film 235 is formed on the insulating film 220. Next, as shown in FIGS. 8A and 8B, an interlayer insulating film 240b, and a p-type semiconductor film 250 serving as a p-type thermo-electric device 251 are formed on the intermediate product 200a formed with the n-type semiconductor film 230. Next, as shown in FIGS. 9A and 9B, the conductive film 270 is formed after contact holes H21 to H24 are formed in the interlayer insulating film 240b, and an interlayer insulating film formed on the intermediate product 200b formed with the p-type semiconductor film 250. Accordingly, similar to the first embodiment, a hot junction connection line 271, a cold junction connection line 272, a signal output electrode 273, a thermopile connection line 274, a heater energization electrode 275, and a ground wiring line 276 are formed, and a heater 278, a heater wiring line 279 that connects the heater 278 to the ground wiring line 276, and the soaking films MS1 to MS3 are formed. In addition, the shapes of the soaking films MS1 to MS3 are capable of being variously changed. For example, the two soaking film MS1 and MS3 may be continuously formed outside the hot junction connection line 271 so as to surround the hot junction connection line 271, and may surround the hot junction connection line 271 with a narrow gap, similar to the soaking film 177 of the first embodiment.

Moreover, it is also possible to form the soaking film between lines of the heater 278.

Figure 10A:
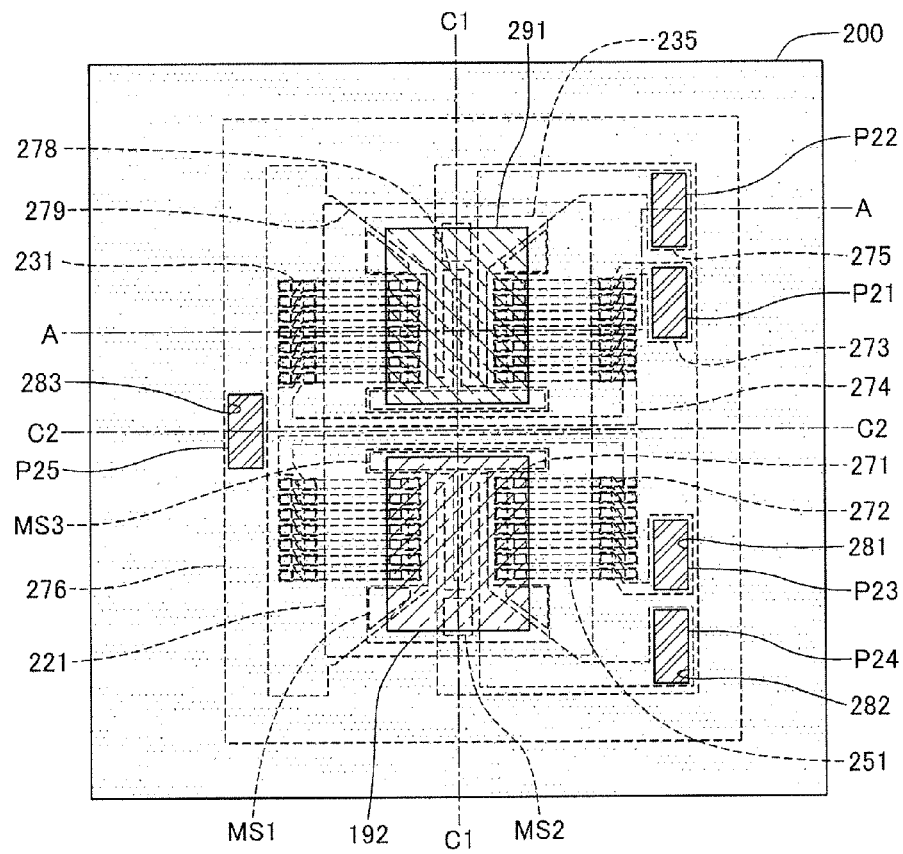
FIGS. 10A and 10B are a plan view and a sectional view showing the gas sensor of the second embodiment manufactured in a process after the manufacturing process shown in FIGS. 9A and 9B.
Figure 10B:
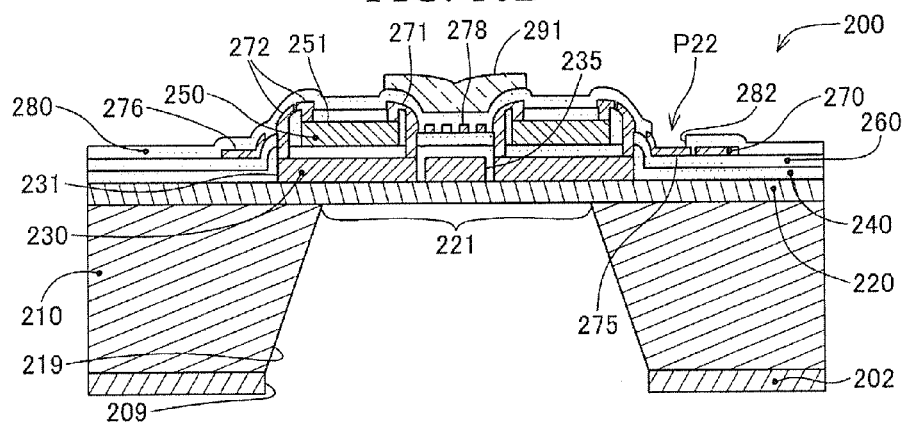

As shown in FIGS. 9A and 9B, after the conductive film 270 is formed, as shown in FIGS. 10A and 10B, a protective film 280 provided with openings 281 to 283 is formed on the intermediate product 200c. Accordingly, signal output pads P21 and P23 from which the signal output electrode 273 is exposed, heater energization pads P22 and P24 from which the heater energization electrode 275 is exposed, and a ground pad P25 from which the ground wiring line 276 is exposed are formed on the top surface of the gas sensor 200. Then, a membrane 221 in which the insulating film 220 is exposed on the back side is formed by forming a cavity 219 provided in the substrate 210 through etching using the mask film 202 provided with an opening 209 as a mask. Next, the gas sensor 200 of the second embodiment is obtained by forming the gas reaction film 291 and the reference film 292 on the protective film 280.

As shown in FIGS. 10A and 10B, even in the gas sensor 200 of the second embodiment, similar to the gas sensor 100 of the first embodiment, all of the hot junction connection line 271 that forms the hot junction, the soaking films 235 and MS1 to MS3, the gas reaction film 291 and the reference film 292, and the heater 278 are formed so as to be located on the membrane 221. Additionally, the cold junction connection line 272 that forms the cold junction is formed so as to be located in a substrate region where the substrate 210 remains.

Meanwhile, the gas sensor 200 of the second embodiment has the soaking film 235 formed as the n-type semiconductor film 230 that is a first soaking portion, and the soaking films MS1 to MS3 and the hot junction connection line 271 that are formed as the conductive film 270 that is a second soaking portion. Then, the heater 278 is formed as the conductive film 270, similar to the soaking films MS1 to MS3 and the hot junction connection line 271. Therefore, since the heater 278 is located between a region where the first soaking portion is formed and a region where the second soaking portion is formed in a lamination direction of the respective functional films, it can be said that the heater 278 is formed between the first and second soaking portions.

In this way, even in the gas sensor 200 of the second embodiment, a situation in which the temperature unevenness occurs in the gas reaction film 291 and the reference film 292 can be limited by providing the soaking portion. Therefore, since the increase in offset or the increase in drift is limited, it is possible to detect the inflammable gas with higher sensitivity, and the measurement reproducibility of the gas concentration can be made high. Additionally, the degradation of the detection sensitivity of the inflammable gas and the degradation of the selectivity can be limited by limiting the temperature unevenness in the gas reaction film 291.

Additionally, in the second embodiment, the first soaking portion is formed of the n-type semiconductor, and the second soaking portion is formed of metal. Therefore, the first soaking portion can be formed simultaneously with the n-type thermo-electric device 231, and the second soaking portion can be formed simultaneously with the wiring lines of the respective portions of the gas sensor 200. Therefore, since it becomes unnecessary to separately provide the processes for forming the first and second soaking portions, the manufacturing process of the gas sensor 200 having the two soaking portions can be further simplified. In addition, the first soaking portion is formed of the p-type semiconductor. Even in this case, since the first soaking portion can be formed simultaneously with the p-type thermo-electric device 251, the manufacturing process of the gas sensor 200 can be further simplified. Additionally, generally, both of the n-type semiconductor film 230 made of a semiconductor and the conductive film 270 made of metal have toughness higher than that of the membrane 221. Thus, damage of the gas sensor 200 after the manufacturing process or completion is limited by providing the two soaking portions.

Moreover, since the hot junction connection line 271 that forms the hot junction and the first and second soaking portions are formed by patterning techniques used in semiconductor manufacturing processes, such as photolithography, the precision of the position of the hot junction with respect to the two soaking portions can be made high. Therefore, even when there is a variation in the formation position of the gas reaction film 291, or a variation in the heat transferred to a plurality of hot junctions, respectively, it is possible to prevent the properties of the gas sensors 200, such as the offset, the drift, or the sensitivity, from varying individually.

Meanwhile, in the gas sensor 200 of the second embodiment, the first and second soaking portions are provided, and the heater 278 is provided between these two soaking portions. Therefore, since the heat generated by the heater 278 is decentralized more uniformly than the gas sensor 100 of the first embodiment provided with the single soaking portion, the temperature unevenness in the gas reaction film 291 and the reference film 292 can be more effectively limited.

C. Modification Examples

The invention is not limited to the above respective embodiments, and can be carried out in various aspects without departing from the scope of the invention. For example, the following modifications can also be made.

C1. Modification Example 1

In the above respective embodiments, in order to reduce the number of manufacturing processes, the soaking portion is formed simultaneously with constituent elements of a circuit that measures the temperatures of the gas reaction film 191 or 291 and the reference film 192 or 292 by forming the soaking portion as the conductive film 170 or 270 and the n-type semiconductor film 230. However, the soaking portion may be formed separately from these constituent elements. Specifically, for example, a metal film may be formed on the protective film as the soaking portion, and the gas reaction film and the reference film may be formed on the metal film. Even in this case, it is noted herein that, in order to limit that the properties of gas sensors vary individually, it is preferable to form soaking portions through the patterning techniques used in semiconductor manufacturing processes, such as photolithography.

C2. Modification Example 2

In the first embodiment, the soaking portion is formed between the heater 132, and the gas reaction film 191 and the reference film 192. Additionally, in the second embodiment, the first soaking portion is formed on the membrane 221, and the second soaking portion is formed such that the heater 278 is located between the first and second soaking portions. However, the position(s) where the soaking portion(s) is (are) formed are not necessarily limited to this (these). Generally, at least one soaking portion may be formed between the membrane, and the gas reaction film and the reference film. Even in this way, a situation in which the temperature unevenness occurs in the gas reaction film and the reference film can be limited by the formed soaking portion.

C3. Modification Example 3

In the above respective embodiments, the soaking portion is formed only in the vicinity of the gas reaction film 191 or 291 and the reference film 192 or 292 on the membrane 121 or 221. However, the region where the soaking portion is formed is not limited to the vicinity of the gas reaction film 191 or 291 and the reference film 192 or 292. Generally, if the soaking portion is located on the membrane 121 or 221 each of the gas detecting portion having the gas reaction film 191 or 291 and the compensating portion having the reference film 192 or 292, the soaking portion can be formed at arbitrary ranges.

Additionally, a soaking portion for a cold junction may be formed at least at one position of positions above, below, and in the vicinity of the cold junction connection line 172 or 272 (refer to FIG. 5A and FIG. 5B). If the soaking portion for a cold junction is provided, variations in the properties of individual gas sensors can be limited because the temperature unevenness between cold junctions is reduced. In this case, openings may be provided in the insulating film 120 or 220 and the protective film 180 or 280, and the soaking portion for a cold junction may be connected to the substrate 110 or 210. If the soaking portion for a cold junction is connected to the substrate 110 or 210, it is possible to further reduce the temperature unevenness between cold junctions.

C4. Modification Example 4

In the above respective embodiments, the temperatures of the gas reaction film 191 or 291 and the reference film 192 or 292 are measured by the hot junctions of the thermopiles that serially connect the thermocouples. However, the temperatures of the gas reaction film 191 or 291 and the reference film 192 or 292 can also be measured using other temperature-measuring elements, such as a hot junction of a single thermocouple, a resistance temperature sensor, or a thermistor. It is noted herein that it is preferable to measure the temperatures of the gas reaction film 191 or 291 and the reference film 192 or 292 using the hot junctions of the thermopiles so that sufficiently high voltage signals showing the temperatures are directly output and it becomes easy to make the detection sensitivity of the inflammable gas higher.

C5. Modification Example 5

In the above respective embodiments, the compensating portion is formed with the reference film 192 or 292 including the carrier that does not carry the combustion catalyst. However, in order to simplify the manufacturing process, it is also possible to omit the formation of the reference film 192 or 292. In this case, the cold junction CJ that is a temperature-measuring element of the compensating portion just has to be formed in the vicinity of the heater 172 so as to measure the temperature of the heater 172 that becomes close to the gas reaction film 191. In addition, in this case, it can be said that the heater 172 of the compensating portion is formed in a region including the vicinity of the temperature-measuring element (cold junction CJ) of the compensating portion. It is noted herein that it is preferable to form the reference film 192 so that the heat capacities of the regions where the reference film 192 and the gas reaction film 191 are formed are brought closer to each other and the degradation of the detection precision of the inflammable gas under the influence of an air current or the like can be limited.

C6. Modification Example 6

In the above respective embodiments, the gas detecting portion having the gas reaction film 191 or 291, and the compensating portion having the reference film 192 or 292 are provided on the gas sensor 100 or 200. However, it is also possible to omit the compensating portion. Even in this case, the temperature unevenness in the gas reaction film is limited. Thus, the degradation of the detection sensitivity of the inflammable gas and the degradation of the selectivity can be limited. Additionally, similar to the first and second embodiments, the damage of the gas sensor after the manufacturing process or completion is limited, and the variations in the properties of individual gas sensors, such as the offset, the drift, or the sensitivity, can be limited.

C7. Modification Example 7

In the above respective embodiments, the cavity 119 or 219 provided in the substrate 110 or 210 itself or the cavity formed in the substrate is used as the heat-insulating portion. However, the heat-insulating portion is not necessarily the cavity. The heat-insulating portion can be formed, for example, by embedding a heat insulating material, such as a porous material or resin, in the cavity provided in the substrate itself. When the $SiO_2$ is used as the porous material, porous $SiO_2$ can be embedded in the cavity by well-known techniques of forming a low relative dielectric constant (Low-k) insulating film or silica aerogel. When the resin is used as the porous material, it is sufficient if the cavity is filled with a monomer or a prepolymer of the resin, and then the monomer or the prepolymer is polymerized by heat or ultraviolet rays. Additionally, as the heat-insulating portion, a heat insulating film, such as a porous material or resin, may be formed on the substrate. In this case, similar to the process of forming the cavity in the above-described substrate, the heat-insulating portion can be formed by forming the heat insulating film, such as a porous material or resin, on the substrate or the insulating film 120 or 220, and making the formed heat insulating film remain thereon. Additionally, a polysilicon film for forming the heat insulating film on the substrate may be formed, and the polysilicon film may be made porous by anodic oxidation. Moreover, as the heat-insulating portion, a porous portion may be formed in the substrate itself. The porous portion can be formed by making a region equivalent to the cavity porous through anodic oxidation from the bottom surface side of the substrate or the top surface side of the substrate, similar to the process of forming the cavity in the substrate itself, when, for example, a Si substrate is used as the substrate. In addition, when the heat-insulating portion that is not the cavity is used and the material of the heat-insulating portion has conductivity, an insulating film is added between the heat-insulating portion and a semiconductor film or a conductive film. The damage of the functional films formed on the heat-insulating portion is suppressed by using the heat-insulating portion, which is not the cavity, in this way.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A catalysis combustion type gas sensor that detects an inflammable gas, comprising:
   a substrate;
   a heat-insulating portion;
   a heater that is formed on the heat-insulating portion;
   a gas reaction film that is formed on the heater and includes a carrier carrying a combustion catalyst for the inflammable gas;
   a temperature-measuring element that is formed in the vicinity of the gas reaction film on the heat-insulating portion; and
   a soaking portion that is formed on the heat-insulating portion and is arranged between the heat-insulating portion and the gas reaction film, the soaking portion being made of high thermal conductivity material and covering an entire area of the gas reaction film in a plane view of the gas reaction film,
   wherein the soaking portion is configured so as to decentralize heat transferred to the soaking portion in the entire soaking portion.

2. The catalysis combustion type gas sensor according to claim 1, wherein the soaking portion has first and second soaking portions that are separately formed, and wherein the heater is arranged between the first soaking portion and the second soaking portion.

3. The catalysis combustion type gas sensor according to claim 1, wherein the temperature-measuring element is a hot junction including first and second thermo-electric devices formed of mutually different materials, and wherein the soaking portion is formed of the same material as that of the first thermo-electric device.

4. The catalysis combustion type gas sensor according to claim 1, wherein the soaking portion is formed of metal.

5. The catalysis combustion type gas sensor according to claim 1, further comprising: a second heater that is formed on the heat-insulating portion, and a reference film that is formed on the second heater on the heat-insulating portion and includes a carrier that does not carry the combustion catalyst for the inflammable gas, a second temperature-measuring element that is formed in the vicinity of the reference film on the heat-insulating portion, and a second soaking portion that is formed on the heat-insulating portion and is arranged between the heat-insulating portion and the reference film, and wherein the second soaking portion is configured so as to decentralize the heat transferred to the second soaking portion in the entire second soaking portion.

* * * * *